(12) United States Patent
Zhang et al.

(10) Patent No.: US 12,232,528 B2
(45) Date of Patent: Feb. 25, 2025

(54) CARTRIDGE AND ATOMIZER HAVING SAME

(71) Applicant: Shenzhen First Union Technology Co., Ltd., Guangdong (CN)

(72) Inventors: Yunkai Zhang, Guangdong (CN); Zhengfa Li, Guangdong (CN); Zhongli Xu, Guangdong (CN); Yonghai Li, Guangdong (CN)

(73) Assignee: Shenzhen First Union Technology Co., Ltd., Shenzhen (CN)

( * ) Notice: Subject to any disclaimer, the term of this patent is extended or adjusted under 35 U.S.C. 154(b) by 164 days.

(21) Appl. No.: 18/053,381

(22) Filed: Nov. 8, 2022

(65) Prior Publication Data

US 2023/0062406 A1     Mar. 2, 2023

Related U.S. Application Data

(63) Continuation of application No. 16/664,623, filed on Oct. 25, 2019, now Pat. No. 11,528,940.

(30) Foreign Application Priority Data

Oct. 26, 2018  (CN) .......................... 201821763876.1

(51) Int. Cl.
*A24F 40/44* (2020.01)
*A24F 40/10* (2020.01)
(Continued)

(52) U.S. Cl.
CPC ............. *A24F 40/44* (2020.01); *A24F 40/46* (2020.01); *A61M 11/042* (2014.02); *A24F 40/10* (2020.01)

(58) Field of Classification Search
CPC .......... A24F 40/10; A24F 40/44; A24F 40/46; A61M 11/042
See application file for complete search history.

(56) References Cited

U.S. PATENT DOCUMENTS 5,895,602 A * 4/1999 Pralus ....................... F24C 7/06
                                                      219/731
9,814,269 B2 * 11/2017 Li ............................. H05B 3/44
(Continued)

FOREIGN PATENT DOCUMENTS

| CN | 107713022 A | 2/2018 |
|----|-------------|--------|
| CN | 108308716 A | 7/2018 |
| EP | 3188570 A2  | 7/2017 |

*Primary Examiner* — Abdullah A Riyami
*Assistant Examiner* — Thang H Nguyen
(74) *Attorney, Agent, or Firm* — Proi Intellectual Property US

(57) ABSTRACT

A cartridge and an atomizer having the cartridge are provided. The cartridge includes a micro-porous body with an absorption surface and an atomization surface; a heating element is embedded in the micro-porous body; the heating element is disposed between the absorption surface and the atomization surface; the heating element includes a first surface and a second surface; the heating element is bored with multiple spaced through holes, the through holes are extending from the first surface to the second surface. The heating element includes a tube-shaped or a flake-shaped structure with an even thickness. An axial direction of the through holes is parallel with a direction of liquid conduction between the absorption surface and the atomization surface.

20 Claims, 7 Drawing Sheets

(51) Int. Cl.
*A24F 40/46* (2020.01)
*A61M 11/04* (2006.01)

(56) References Cited

U.S. PATENT DOCUMENTS

| | | | | |
|---|---|---|---|---|
| 10,517,331 | B2* | 12/2019 | Atkins | A24F 40/53 |
| 10,701,977 | B2* | 7/2020 | Crowe | A24F 40/44 |
| 10,973,262 | B2* | 4/2021 | Li | C04B 35/00 |
| 11,122,835 | B2* | 9/2021 | Alarcon | A24F 40/44 |
| 11,122,836 | B2* | 9/2021 | Jiang | A24F 40/485 |
| 2015/0272218 | A1* | 10/2015 | Chen | A61M 15/06 |
| | | | | 131/329 |
| 2015/0305408 | A1* | 10/2015 | Liu | H05B 3/06 |
| | | | | 392/404 |
| 2015/0359262 | A1* | 12/2015 | Liu | C04B 35/6263 |
| | | | | 264/681 |
| 2016/0106153 | A1* | 4/2016 | Zhu | A24F 40/46 |
| | | | | 392/404 |
| 2017/0224018 | A1* | 8/2017 | Li | A24F 40/46 |
| 2017/0251729 | A1* | 9/2017 | Li | A24F 40/485 |
| 2019/0124993 | A1* | 5/2019 | Matsumoto | H05B 1/0297 |
| 2019/0246692 | A1* | 8/2019 | Li | A24F 1/00 |
| 2021/0084983 | A1* | 3/2021 | Buchberger | A24F 40/46 |
| 2021/0289833 | A1* | 9/2021 | Moloney | A24F 40/46 |

* cited by examiner

CARTRIDGE AND ATOMIZER HAVING SAME

CROSS REFERENCE TO RELATED APPLICATIONS

The present application is a continuation application of U.S. patent application Ser. No. 16/664,623, which claims priority to Chinese Patent Application CN 201821763876.1 filed on Oct. 26, 2018. The content of U.S. Ser. No. 16/664,623 and CN 201821763876.1 is hereby incorporated by reference herein as if set forth in its entirety.

TECHNICAL FIELD

The present disclosure relates to the field of atomizers, and in particular to a cartridge and an atomizer having same.

BACKGROUND ART

The electronic cigarette products are realized to rapidly atomizing liquid by a cartridge allocated therein, so performances and characteristics of the cartridge are directly influences the atomizing effect on the liquid. The prior art cartridge is typically composed of a liquid conductive element and a heating wire carried on the liquid conductive element. As used herein, the liquid conductive element absorbs liquid by a surface of the liquid conductive element contacting a reservoir formed in the atomizer to absorb the liquid then conducted to the heating wire via micro-pores therein and then heated by the heating wire to form an aerosol inhaled by the smokers.

The previous heating wire in the atomizer directly contacts the cotton or the heating wire is half exposed to outside of the liquid conductive element. However, in one aspect, when a power of the heating wire is increased or the heating wire doesn't contact the liquid completely, it is easy to generate burnt flavor. In another aspect, in the aerosol that contain some shredded pieces of cotton fibers, carbide fibers or metal particles in the heating wire itself, which is adverse to the human's health.

To eliminate the above shortages, multiple improved atomizers are proposed and adopted, such as Chinese patent CN201711069939.3 filed by SHENZHEN INNOKIN ELECTRONIC TECH CO LTD relates to a structure of an atomizer including a main body of power metallurgy and a heating wire after insulation treatment, and the heating wire is embedded into the main body of power metallurgy. As used herein, the main body of power metallurgy includes a micro-porous liquid conductive element formed by sintering metal powers. In addition, Chinese patent CN201810150677.1 filed by SHENZHEN SMOORE TECHNOLOGY LTD relates to an electronic cigarette and a heating element thereof, the heating element includes a porous body for absorbing liquid and at least one heating element for aerosolizing the liquid carried on the porous body; the at least one heating element includes an elongate strip-shaped heating part, part of the heating part is embedded in the micro-porous body. By replying on embedment and segments, the micro-porous body is prevented from dry burn to realize absorption and atomization of the liquid, leading to more pure taste of the aerosol.

However, when using the above structure, after the heating wire is embedded, the heat generated by the heating wire will be absorbed and conducted more rapidly, and the amount of liquid contacting the heating wire gets decreased to cause the atomizing efficiency and the atomizing amount to be reduced, particles of the aerosol are smaller thereby weakening the throat hit.

SUMMARY

To overcome the above drawbacks to the cartridge, the present disclosure generally relates to a cartridge without dry burn and metal pollution, having a stable amount of aerosol.

In a first aspect, the present disclosure provides a cartridge including a micro-porous body with an absorption surface and an atomization surface, and a heating element embedded in the micro-porous body; the heating element disposed between the absorption surface and the atomization surface; the heating element having a first surface and a second surface opposite with each other; the heating element bored with multiple spaced through holes extending from the first surface to the second surface. Preferably, the heating element includes a tube-shaped or a flake-shaped structure with an even thickness. Preferably, the axial direction of the through holes is parallel with the direction of liquid conduction between the absorption surface and the atomization surface. The axial direction of the through hole may also be perpendicular to the direction of the liquid conducting from the absorption surface to the atomization surface.

Preferably, sizes of the through holes are in a range of 0.1~0.5 mm. That is, diameters of the through holes are in a range of 0.1~0.5 mm.

Preferably, a distance from the heating element to the atomization surface is in a range of 0.2~2 mm along a direction of the absorption surface towards the atomization surface.

Preferably, the heating element includes a strip-shaped structure to be wound as a spiral.

Preferably, the micro-porous body comprises a first micro-porous body and a second micro-porous body.

Preferably, the heating element is disposed between the first micro-porous body and the second micro-porous body.

Preferably, the absorption surface is formed on the first micro-porous body, the atomization surface is formed on the second micro-porous body.

Preferably, a heat conductive rate of the first micro-porous body is higher than that of the second micro-porous body;

Preferably, the first micro-porous body includes a first micro-porous material, the second micro-porous body includes a second micro-porous material; a heat conductive rate of the first micro-porous material is higher than that of the second micro-porous material.

Preferably, the first micro-porous body has a first porosity, the second micro-porous body has a second porosity; the first porosity is less than the second porosity;

Preferably, a thickness of the heating element is in a range of 0.1 mm~0.15 mm.

The present disclosure further relates to an atomizer including an atomizing sleeve, the atomizing sleeve has a reservoir formed therein; the atomizing sleeve has a cartridge therein configured for atomizing liquid, such as (but not limited to) tobacco liquid; as used herein, the cartridge is according to the above cartridges.

In embodiments in the present disclosure, by replying on the heating element embedded in the micro-porous body and further through holes provided thereon, they guides the aerosol to be converged along the transversal and longitudinal directions and the aerosol bubble to grow bigger since oscillation and fusion in an aerosolizing process, thus improving particle sizes of the aerosol and changing the power of the heating element, thereby improving the heating efficiency and improving the aerosol amount.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Provided herein are a cartridge mainly applied to an electronically-operated aerosol-generating article (alternatively referred to as vaporization devices or electronic vaping devices etc.) that generally heats a liquid aerosolizable material (such as (but not limited to) tobacco liquid) containing nicotine to generate an aerosol, eventually drawn by the users. Taking the electronic cigarette as an example in the present disclosure hereinafter, the cartridge typically includes a micro-porous body and a heating element, of course including other functional components, as well as overall design and assembly way to be concerned.

Figure 1:
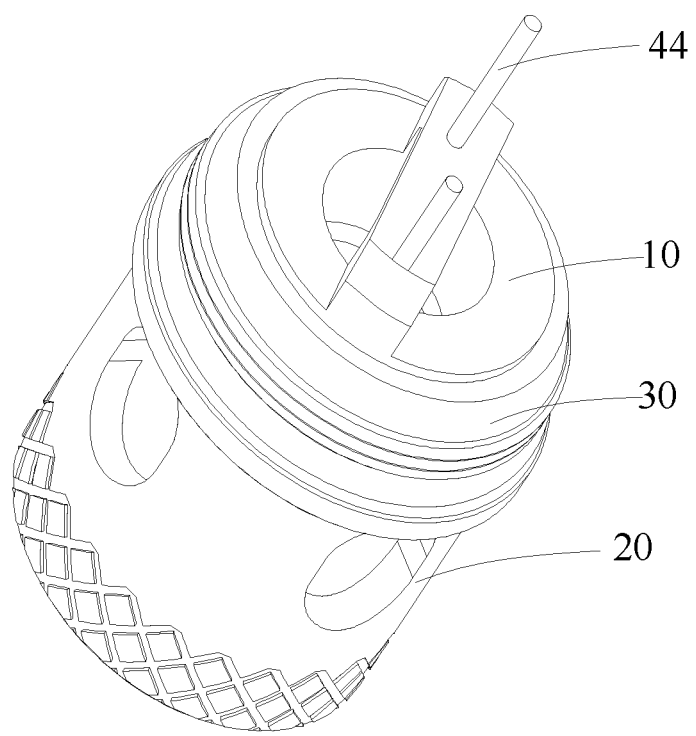
FIG. 1 is an isometric view of the cartridge after assembled according to an embodiment of the present disclosure.
Figure 2:
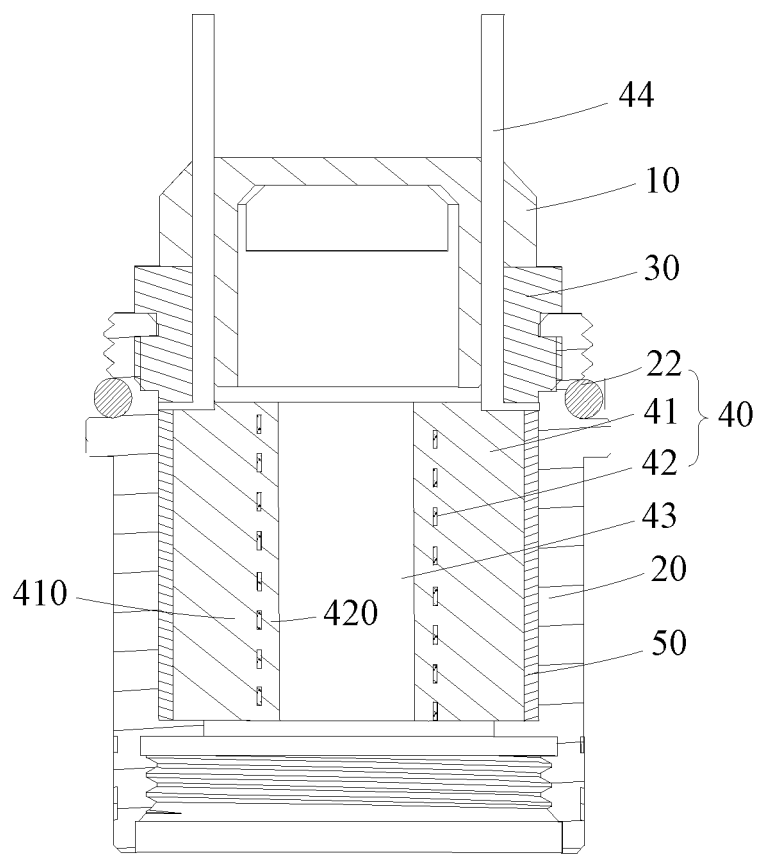
FIG. 2 is a cross-sectional view of the cartridge in FIG. 1.
Figure 3:
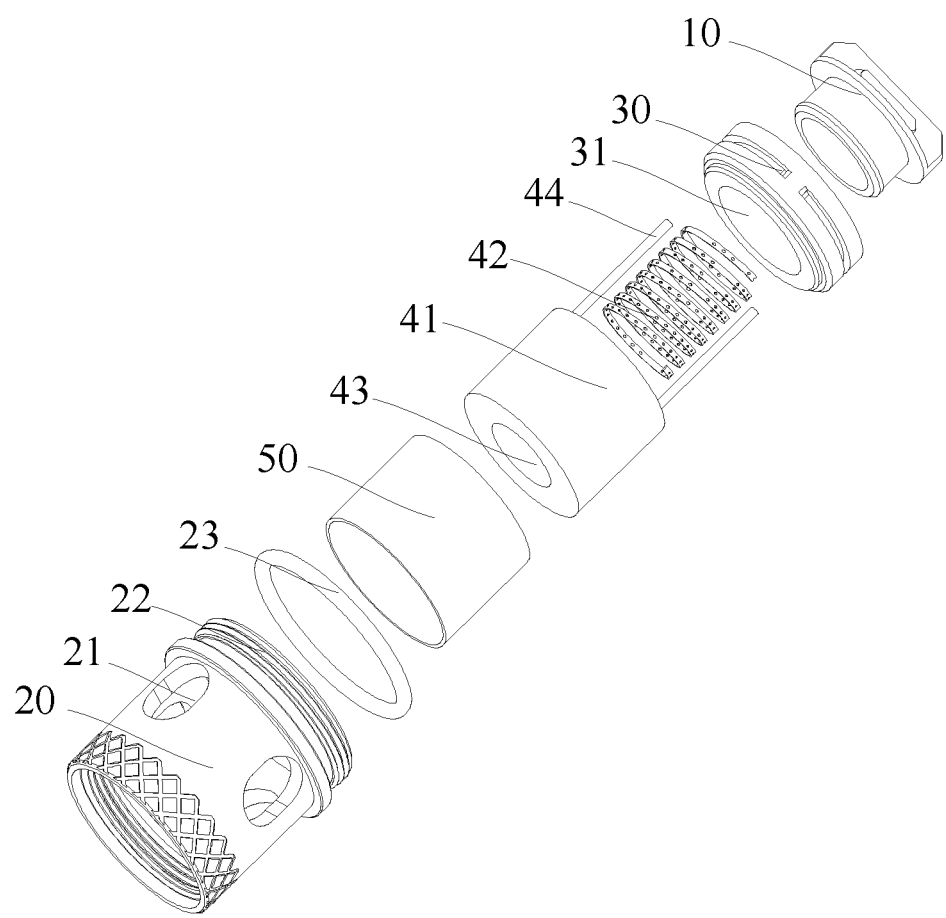
FIG. 3 is an exploded view of the cartridge before assembled in FIG. 2.

Referring to FIG. 1 to FIG. 3, FIG. 1 is an isometric view of the cartridge after assembled according to an embodiment of the present disclosure; FIG. 2 is a cross-sectional view of the cartridge in FIG. 1; FIG. 3 is an exploded view of the cartridge before assembled in FIG. 1. In this embodiment, the structure of the atomizer includes a conductive lid 10 and a conductive sleeve 20. According to FIG. 1 and FIG. 3, the conductive lid 10 is shaped as a lid at a proximal end of the atomizer, the conductive sleeve 20 is roughly a hollow cylinder at a distal end of the atomizer. The conductive lid 10 covers an opening formed on a proximal surface of the conductive sleeve 20. Ultimately when assembling other modules of the electronic cigarette, the conductive lid 10 and the conductive sleeve 20 are respectively coupled with the anode and cathode electrodes of the power supply to form a loop along with the heating element in the cartridge. Therefore, if applicable, the conductive lid 10 and the conductive sleeve 20 are both made by electrically conductive materials, generally metal conductive materials adopted.

To avoid the conductive lid 10 and the conductive sleeve 20 to be directly conducted, between the conductive lid 10 and the conductive sleeve 20 defines a circular insulator 30 bored with a mounting hole 31. In accordance with characteristics of the conductive lid 10 covering the conductive sleeve 20, the insulator 30 is designed as a circular shape and mounted over the opening of the conductive sleeve 20, next the conductive lid 10 is mounted to cover the insulator 30.

To further prompt the atomization of liquid, an atomization component 40 is disposed inside a chamber of the conductive sleeve 20. The atomization component 40 includes a hollow micro-porous body 41 and a heating element 42 embedded in the micro-porous body 41.

As used herein, a contour of the micro-porous body 41 is matched with the chamber of the conductive sleeve 20, which is cylindrical. Inside of the micro-porous body 41 has an air flow path 43 configured for outputting the aerosol generated by the heating element 42.

Figure 4:
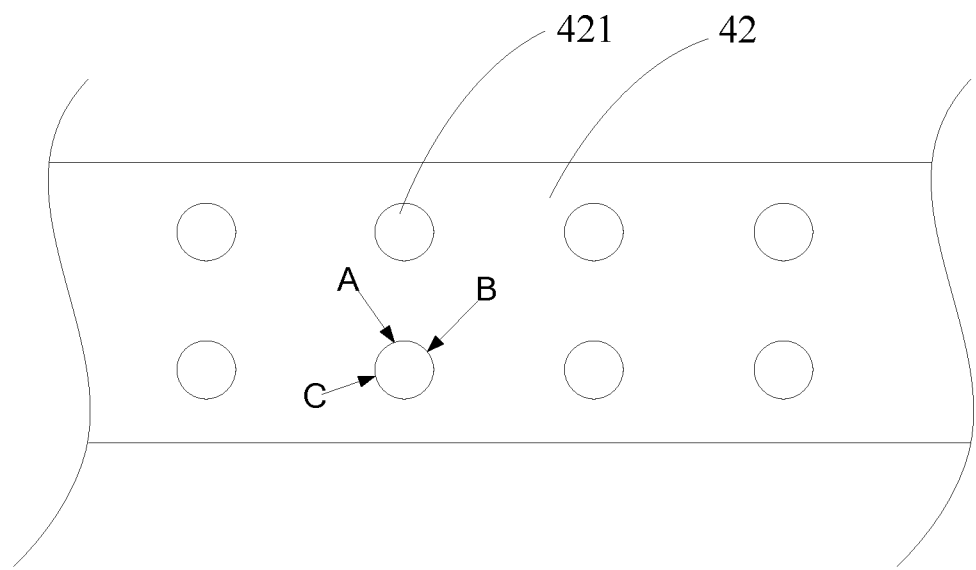
FIG. 4 illustrates part of the heating element unfolded in FIG. 3.
Figure 5:
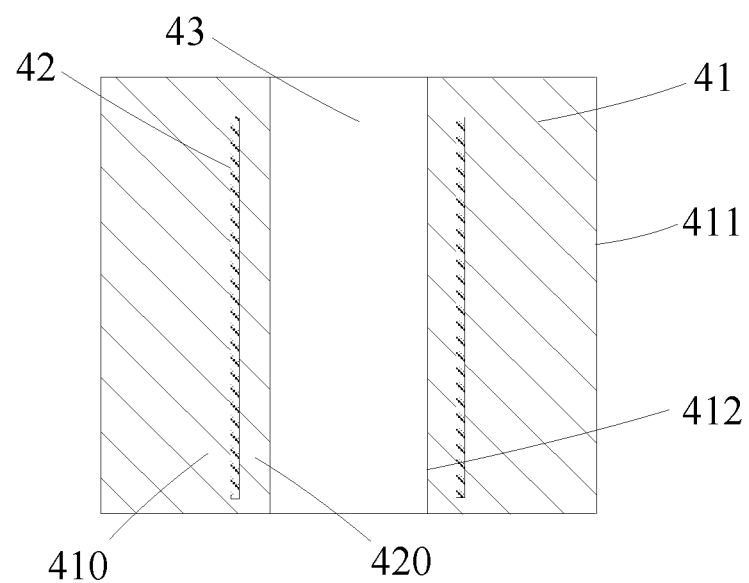
FIG. 5 is a cross-sectional view of the cartridge incorporating the micro-porous body and the heating element assembled according to another embodiment of the present disclosure.

In the embodiments of the present disclosure, FIGS. 2 to 5 are relative with the aerosol flowing and the atomization. FIG. 5 is a cross-sectional view of the cartridge incorporating the micro-porous body and the heating element assembled according to another embodiment of the present disclosure. Along a radial direction, an outer surface of the micro-porous body 41 works as an absorption surface 411 configured for absorbing liquid stored in the reservoir, an inner surface of the micro-porous body 41 works as an atomization surface 412, the aerosol after atomization of the liquid is expelled from the atomization surface 412 to the air flow path 43 at the center. The micro-porous body 41 itself has the micro-porous structure for conveying the liquid that is absorbed by the absorption surface 411 to the heating element 42 via capillary impregnation. Meanwhile, to satisfy that the absorption surface 411 is capable of absorbing liquid, a periphery of the conductive sleeve 20 is bored with liquid conductive holes 21 for allowing the liquid to flow into the conductive sleeve 20, the liquid further is absorbed by the absorption surface 411 of the micro-porous body 41.

The heating element 42 is embedded in the micro-porous body 41, by relying on the heating element 42 entirely embedded in the micro-porous body 41, the liquid doesn't need to be conducted to the surface of the heating element 42, only flowing near to the heating element 42 while starting to be heated and atomized. In one aspect, the heating element 42 and the micro-porous body 41 has thermal contact for preventing dry burn, in another aspect, a majority of the liquid fail to directly contact the heating element 42, which may prevent the heating element 42 from generating metal pollution. Since the heating element 42 is made of stainless steel, Ni—Cr alloy, Fe—Cr—Al alloy, metallic titanium etc., and the material also includes slight metal impurities to release metal particles when heating and contacting the liquid, thereby preventing metal pollution due to too much liquid contact does during atomization.

Furthermore, in the above embodiment, to facilitate the aerosol rapidly flowing into the air flow path 43, the position of the heating element 42 embedded in the micro-porous body 41 may be allocated near the air flow path 43, the embedding depths are in a range of 0.2~2 mm, that is distances between the heating element 42 and the atomization surface (that is the inner surface of the micro-porous body 41) are in a range of 0.2~2 mm.

Figure 6:
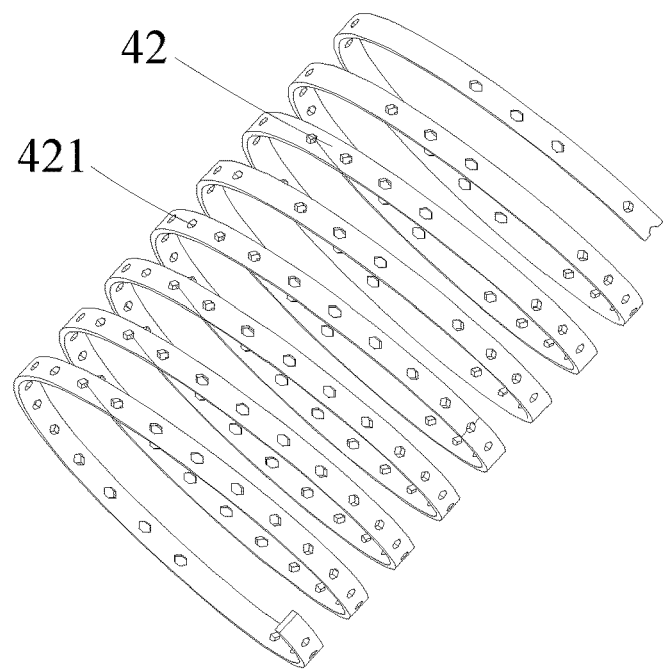
FIG. 6 is an isometric view of the heating element in FIG. 3.
Figure 7:
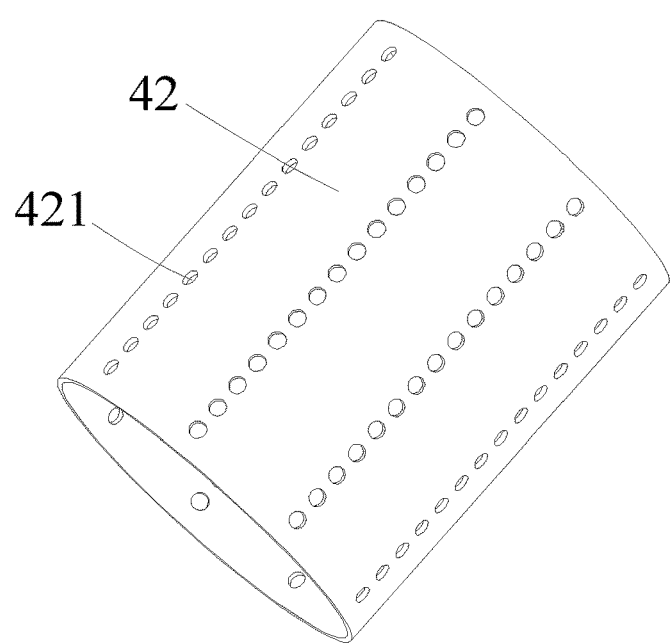
FIG. 7 is an isometric view of the heating element according to another embodiment of the present disclosure.
Figure 8:
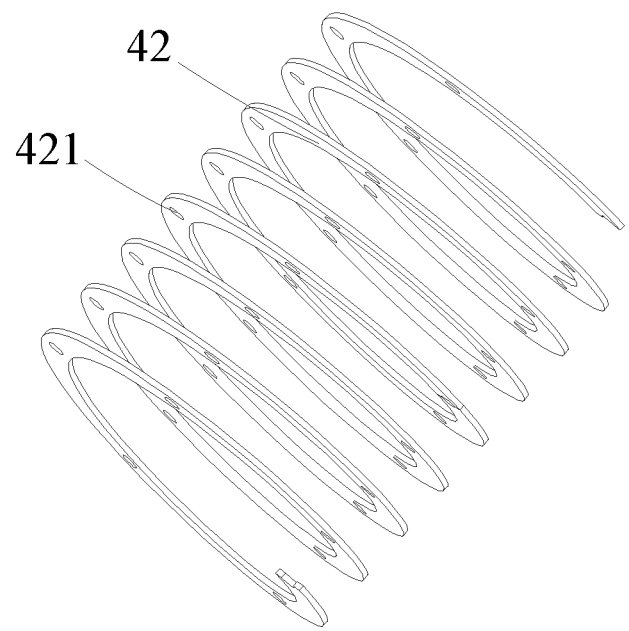
FIG. 8 is an isometric view of the heating element according to the other embodiment of the present disclosure.
Figure 9:
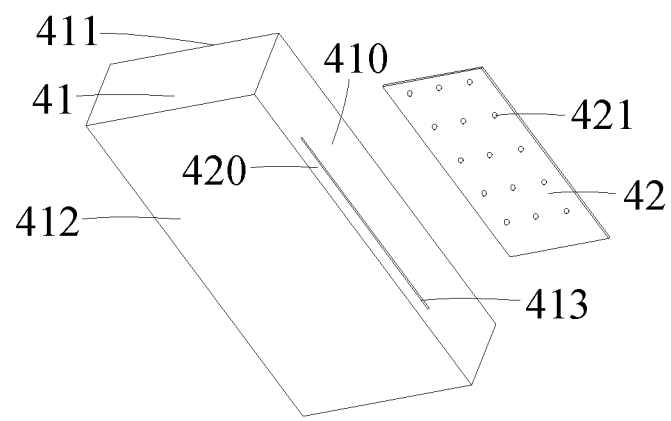
FIG. 9 is an isometric view of the cartridge incorporating the micro-porous body and the heating element assembled according to another embodiment of the present disclosure.
Figure 10:
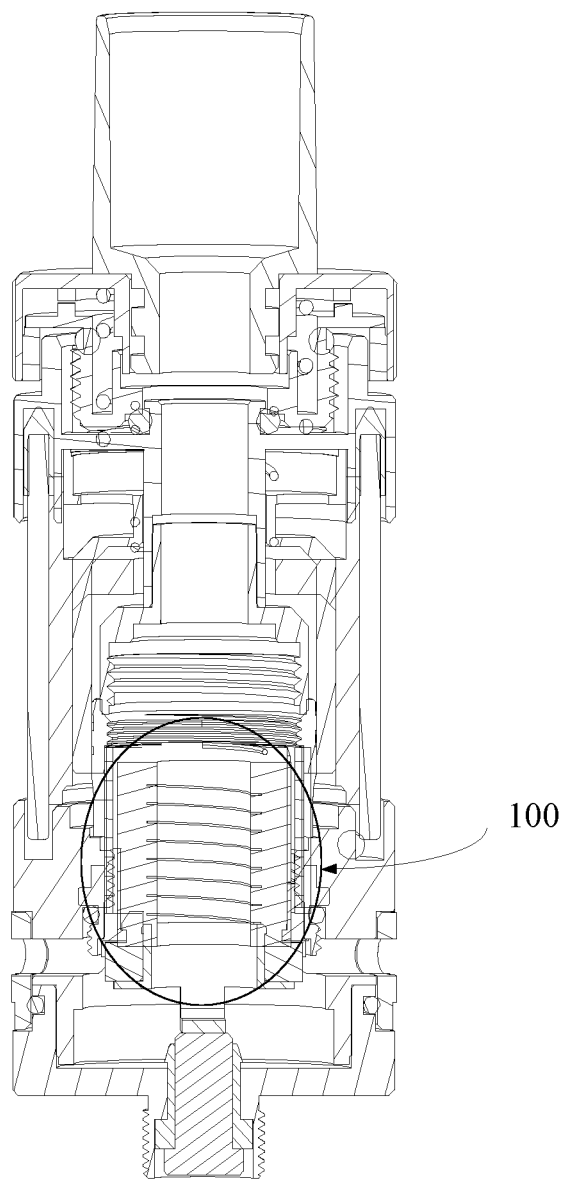
FIG. 10 is an isometric view of the atomizer incorporating the cartridge according to one embodiment of the present disclosure.

A shape of the heating element 42 is defined with numerous convenient shapes, such as a spiral flake shape or other shapes in FIG. 6 to FIG. 8. In order to improve the particle sizes of the aerosol, the heating element 42 is bored with through holes 421 extending from the first side surface to the second side surface. The through holes 421 provided are different from an intention of improving a resistance to bore holes on the heating wire, adopting small-sized holes for changing a liquid contacting way when liquid particles contacts the heating element 42, that is three-dimensional contact, not surface to surface contact. Thus, the oscillation and fusion of the liquid within the through holes make the aerosol particles bigger, leading to strong throat hit. If applicable, the diameters of the through holes 421 are in a range of 0.1~0.5 mm, which prevents too big sized through holes 421 thereby lacking oscillation of the liquid.

Furthermore, the oscillation of the liquid in the through holes 421 may refer to FIG. 4, FIG. 4 illustrates part of the heating element unfolded in FIG. 3. By replying on appropriate sized through holes 421, the heating element 42 is changed such that current paths diverge or converge on sites near to through holes 421, since different sites have different temperatures based on different currents. More specifically, in FIG. 4, since the heating element 42 is bored with numerous through holes 421, after two ends of the heating element 42 is electrically coupled with the power supply, in one aspect, the cross-sectional area of the heating element where includes through holes 421 is decreasing, the resistance thereof is getting larger; in another aspect, the divergence and convergence of current around the through holes 421 makes the current distribution uneven around the through hole. Ultimately the heating temperature of different sites around the through holes 421 is changing. As used herein the flavored liquid containing propylene glycol (PG), vegetable glycerin (VG) or other organic based solvent would be atomized at different sites, such as A site in FIG. 4 has a higher temperature; C site has a lower temperature; B site has a mediate temperature. When the liquid contacts the heating element for atomization in the through holes 421, the flavored solvent is atomized to generate a big amount of aerosol particles at C site; vegetable glycerin (VG) is atomized to generate a big amount of aerosol particles at B site; propylene glycol (PG) is atomized to generate a big amount of aerosol particles at A site. Furthermore, since the through holes 421 provide appropriate particle contacting space thereby in the space liquid containing above ingredients will be gradually blended to be big mixing particles. Along with the aerosol is blended with other particles to grow bigger, until inhaled into the mouth, it generates a good throat hit. When there are no through holes 421, the different temperature sites in FIG. 4 are not existed, various ingredients will be atomized towards different widths, until being inhaled into the mouth, with insufficient fusion; and when the through holes 421 are too big, the particles among through holes 421 have larger distances which is difficult for fusion, and eventually the amount of the big-sized aerosol particles are decreased.

Meanwhile, to improve the atomization efficiency and aerosol amount, preferably, an axial direction of the through holes 421 is perpendicular or parallel with a direction of liquid conducting in the micro-porous body 41, as shown in FIG. 6.

Furthermore, since the embedding method of the heating element 42 has a decreasing amount of aerosol compared to an exposure method, to overcome the disadvantage, the micro-porous body 41 is designed as segmentation for an intention to improve the atomization efficiency. More specifically, the heating element 42 embedded in the micro-porous body 41 has different embedding depth, the micro-porous body 41 is separated into a first micro-porous body 410 disposed between the absorption surface 411 and the heating element 42, and a second micro-porous body 420 between the heating element 42 and the atomization surface 412. Meanwhile, the second micro-porous body 420 has a lower heat conductive rate compared to the first micro-porous body 410.

Based on the heat efficiency gradient designs to the micro-porous body 41, and the second micro-porous body 420 itself has low heat conductive rate thereby it is slow to convey heat outside with consequently a certain thermal insulation effect, thus the temperature of the second micro-porous body 420 can be maintained at the atomizing temperature to retain the atomization efficiency. However, the first micro-porous body 410 has a high heat conductive rate thereby it is fast to convey heat outside with consequently less atomization effect and less amount of aerosol, as used herein, the first micro-porous body 410 mainly works as a function of liquid conduction and the atomization process mainly focuses on the second micro-porous body 420 disposed between the heating element 42 and the air flow path 43. In another aspect, since the second micro-porous body 420 directly contacts the air flow path 43, the aerosol would rapidly flow into the air flow path 43 so as to improve the flow efficiency. Additionally, since the second micro-porous body 420 has high atomization efficiency and the liquid is consumed fast, which is in favor of capillary impregnation between the first micro-porous body 410 and the second micro-porous body 420, and accelerating atomization efficiency.

The above micro-porous body 41 having two different heat conductive rates may be realized by multiple methods hereinafter.

In one embodiment, the micro-porous body 41 is made of composite materials, including at least one or more selected form a group of micro-porous ceramic, micro-porous glass ceramic, micro-porous glass, foamed metals, aluminum oxide, silicon carbide, diatomaceous earth and so on in a form of honeycomb rigid ceramic type. Two kinds of heat conductive materials with different heat conductive rates are combined, such as the first micro-porous body 410 includes high heat-conductive-rate materials like foamed metals and micro-porous ceramic etc.; the second micro-porous body 420 includes low heat-conductive-rate materials like micro-porous glass ceramic, micro-porous glass and silicon carbide ceramic etc. With different heat conductive rates, different heat conductive materials form the first micro-porous body 410 and the second micro-porous body 420 to improve atomization.

In another embodiment, an identical material with different porosities is adopted, particularly, the porosity of the second micro-porous body 420 is greater than that of the first micro-porous body 410. For the micro-porous body, the porosity is greater, a relative density thereof is lower thus the heat conductive medium is less thereby the heat conductive efficiency is lower. Obviously, the same material with different porosities defined to form the first micro-porous body 410 and the second micro-porous body 420 may improve atomization efficiency.

Of course, the aforementioned material and porosity may be used together, that is, the first micro-porous body 410 has a higher heat conductive rate than the second micro-porous body 420 while the first micro-porous body 410 has a less porosity than the second micro-porous body 420.

Furthermore, between the micro-porous body 41 and the conductive sleeve 20 has a fibrous element 50 for absorbing and retaining the liquid. When the cartridge doesn't work, if the micro-porous body 41 contains two much liquid, partial liquid leak out along a contact surface of the micro-porous body 41 and the conductive sleeve 20 under the gravity, but after the fibrous element 50 is provided, the leakage of liquid is mitigated. If applicable, the shape of the fibrous element 50 may be designed as a cylindrical sleeve that can entirely covers the periphery of the micro-porous body 41 (i.e. the absorption surface 411); the material of the fibrous element 50 includes cotton fiber, resin fiber and carbon fiber, some flexible fibers.

Meanwhile, in favor of the electrical coupling of the heating element 42, two electrode connecters 44 are carried on the heating element 42. In a process of assembling, after allocating the heating element 42, welding two electrode connecters 44 of the heating element 42 then one is coupled with the conductive lid 10, the other one is coupled with the conductive sleeve 20, thus the whole loop is finished. If applicable, the two electrode connecters 44 include pins that are capable of directly abutting against the conductive lid 10/conductive sleeve 20 to realize coupling. In this way, it is convenient to remove components away for replacement. Of course, in some embodiments, the two electrode connecters 44 are coupled with the conductive lid 10/conductive sleeve 20 via welding.

Furthermore, referring to FIG. 6 and FIG. 8, the heating element 42 includes spiral or tubular shape, which can be changed/modified for an intention to increase atomization efficiency after embedding. Compared to common heating wire with a thickness of 0.03~0.1 mm and a resistance of a few ohms, the thickness of the heating element 42 is increased to 0.1 mm~0.15 mm while the resistance is decreased to 0.4~2.0 ohms. When coupled with the power supply that outputs constant outputted power, the current is increased because of decreased resistance of the heating element 42, eventually the power P=I2*R is increased accordingly leading to improve atomization efficiency.

In use, to tighten the connection of the cartridge and the reservoir and avoid leakage of liquid, the conductive sleeve 20 is provided with a threaded connector 22 for connecting with an inner wall of the atomizing sleeve, further a silicon ring 23 is provided at an end of the threaded connector 22 to improve sealing.

The heating element 42 designed in spiral/tubular shape for matching the shape of hollow micro-porous body 41 after embedded. When the shape of the micro-porous body 41 adopts other rectangular or irregular shapes, the shape of the heating element 42 may be changed accordingly. For instance, in FIG. 8, the micro-porous body 41 is a block, the upper surface is the absorption surface 411, the lower surface is the atomization surface 412, the liquid absorbed by the absorption surface 411 is conveyed towards the atomization surface 411 via micro-porous structure, and the heating element 42 is embedded into the heating element 42 along a mounting seam 413. After embedding, the micro-porous body 41 is divided into two parts, a first micro-porous body is disposed over the heating element 42 (i.e. between the heating element 42 and the absorption surface 411), a second micro-porous body is disposed underneath the heating element 42 (i.e. between the heating element 42 and the atomization surface 411). Or along a direction of the liquid conveyed from the absorption surface to the atomization surface, the micro-porous body 41 includes the first micro-porous body 410 and the second micro-porous body 420, the heating element 42 is disposed between the first micro-porous body 410 and the second micro-porous body 420, the liquid close to the heating element 42 is atomized to form an aerosol expelled from the atomization surface 420. Based on the above description, in FIG. 9, a heat conductive rate of the second micro-porous body 420 is less than that of the first micro-porous body 410, in this way, the atomization efficiency is roughly equal to that when the heating element 42 is exposed of the micro-porous body 41. Additionally, as shown in FIG. 9, the heating element 42 is bored with through holes 421 for oscillation and fusion of liquid particles; and the embedding depth of the heating element 42 underneath the atomization surface 412 is in a range of 0.2~2 mm.

Further, when the micro-porous body 41 in FIG. 9 is adopted, the conductive lid 10 and the conductive sleeve 20 are modified in shapes and structures. More specifically, the conductive sleeve 20 is designed as a hollow block, and a side surface of the conductive sleeve 20 opposite with the absorption surface 411 is bored with liquid conductive holes 21; and the conductive lid 10 is designed to match with the conductive sleeve 20. Of course, to prevent the conductive lid 10 and the conductive sleeve 20 from being directly conducted, an insulation element 30 is provided therebetween, the insulation element 30 could have specialized shapes and mounting methods which should belong to the scope of the protection, without further description herein.

In the embodiments, the heating element is embedded into the micro-porous body, with through holes bored thereon, which prompts mutual gathering of the aerosol from transversal and perpendicular directions. During atomization, the aerosol bubbles are growing bigger to improve the aerosol particles, with improving the heating efficiency of the heating element, therefore improving the amount of aerosol and improving efficiency.

The present disclosure further relates to an atomizer including the above cartridge, as shown in FIG. 10. The atomizer includes an atomizing sleeve, the atomizing sleeve includes an air flow path and a reservoir. The cartridge 100 containing the heating element in FIG. 9 is assembled in the atomizing sleeve for liquid communicating the reservoir to realize conduction and atomization of liquid.

The atomizer in FIG. 10 is suitable for hollow cylindrical porous cartridges along an axial direction thereof. When the block-shaped cartridge in FIG. 9 is adopted, the inner structure of the atomizing sleeve is modified further to match, which is available from the prior art electronic cigarettes, then embedding the heating element in the aforementioned embodiments, finally adjusting the electrode connection for only making sure electricity conduction and heat generation.

The atomizer containing the above cartridge replies on the heating element embedded in the micro-porous body then bored with through holes, promoting mutual gathering of the aerosol from transversal and perpendicular directions. During atomization, the aerosol bubbles are growing bigger to improve the aerosol particles, with improving the heating efficiency of the heating element, therefore improving the amount of aerosol and efficiency.

The illustrated methods are exemplary only. Although the methods are illustrated as having a specific operation flow, two or more operations may be combined into a single operation, a single operation may be performed in two or more separate operations, one or more of the illustrated operations may not be present in various implementations, and/or additional operations which are not illustrated may be part of the methods. In addition, the logic flows depicted in the accompanying figures and/or described herein do not necessarily require the particular order shown, or sequential order, to achieve desirable results. Other implementations may be within the scope of the following claims.

What is claimed is:

1. A cartridge, comprising:
   a micro-porous body with an absorption surface and an atomization surface;
   a heating element embedded in the micro-porous body; the heating element disposed between the absorption surface and the atomization surface;
   wherein the heating element comprises a first surface and a second surface;
   the heating element is bored with multiple spaced through holes; the through holes are extending from the first surface to the second surface;
   wherein the heating element comprises a tube-shaped or a flake-shaped structure with an even thickness; and
   wherein an axial direction of the through holes is parallel with a direction of liquid conduction between the absorption surface and the atomization surface.

2. The cartridge according to claim 1, wherein diameters of the through-holes are in a range of 0.1~0.5 mm.

3. The cartridge according to claim 1, wherein a distance from the heating element to the atomization surface is in a range of 0.2~2 mm along a direction of the absorption surface towards the atomization surface.

4. The cartridge according to claim 1, wherein the heating element comprises a strip-shaped structure to be wound as a spiral.

5. The cartridge according to claim 1, wherein the micro-porous body comprises a first micro-porous body and a second micro-porous body.

6. The cartridge according to claim 5, wherein the heating element is disposed between the first micro-porous body and the second micro-porous body.

7. The cartridge according to claim 5, wherein the absorption surface is formed on the first micro-porous body and the atomization surface is formed on the second micro-porous body.

8. The cartridge according to claim 5, wherein a heat conductive rate of the first micro-porous body is higher than that of the second micro-porous body.

9. The cartridge according to claim 5, wherein the first micro-porous body comprises a first micro-porous material and the second micro-porous body comprises a second micro-porous material; a heat conductive rate of the first micro-porous material is higher than that of the second micro-porous material.

10. The cartridge according to claim 5, wherein the first micro-porous body comprises a first porosity, the second micro-porous body comprises a second porosity; the first porosity is less than the second porosity.

11. The cartridge according to claim 1, wherein a thickness of the heating element is in a range of 0.1 mm~0.15 mm.

12. The cartridge according to claim 1, wherein along a radial direction an outer surface of the microporous body is the absorption surface, and wherein an inner surface of the micro-porous body is the atomization surface.

13. The cartridge according to claim 1, wherein the heating element and the micro-porous body has thermal contact for preventing dry burn.

14. The cartridge according to claim 1, wherein the heating element is embedded in the micro-porous body at a depth in a range of 0.2-2 mm.

15. The cartridge according to claim 1, wherein distances between the heating element and the atomization surface are in a range of 0.2-2 mm.

16. The cartridge according to claim 1, wherein an air flow path is formed inside the micro-porous body configured to output aerosol generated by the heating element.

17. An atomizer comprising:
   an atomizing conductive sleeve;
   the conductive sleeve comprising a reservoir formed therein; the conductive sleeve
   comprising a cartridge therein configured for atomizing the liquid;
   wherein the cartridge comprises
   a micro-porous body with an absorption surface and an atomization surface;
   a heating element embedded in the micro-porous body; the heating element disposed between the absorption surface and the atomization surface;
   wherein the heating element comprises a first surface and a second surface;
   the heating element is bored with multiple spaced through holes; the through holes are extending from the first surface to the second surface;
   wherein the heating element comprises a tube-shaped or a flake-shaped structure with an even thickness; and
   wherein an axial direction of the through holes is parallel with a direction of liquid conduction from the absorption surface to the atomization surface.

18. The atomizer according to claim 17, wherein a contour of the micro-porous body is matched with a chamber of the conductive sleeve.

19. The atomizer according to claim 17, wherein a periphery of the conductive sleeve is bored with liquid conductive holes for allowing liquid to flow into the conductive sleeve.

20. The atomizer according to claim 19, configured to allow the liquid that flows into the conductive sleeve to be absorbed by the absorption surface of the micro-porous body.

* * * * *